US012685672B2

(12) United States Patent
Lin

(10) Patent No.: US 12,685,672 B2
(45) Date of Patent: Jul. 21, 2026

(54) METHOD FOR TREATING TINNITUS

(71) Applicant: NATIONAL CHENG KUNG UNIVERSITY, Tainan City (TW)

(72) Inventor: Chou-Ching Lin, Tainan City (TW)

(73) Assignee: NATIONAL CHENG KUNG UNIVERSITY, Tainan City (TW)

( * ) Notice: Subject to any disclaimer, the term of this patent is extended or adjusted under 35 U.S.C. 154(b) by 593 days.

(21) Appl. No.: 18/298,220

(22) Filed: Apr. 10, 2023

(65) Prior Publication Data

US 2023/0320902 A1    Oct. 12, 2023

Related U.S. Application Data

(60) Provisional application No. 63/328,801, filed on Apr. 11, 2022.

(51) Int. Cl.
A61F 11/00         (2022.01)
(52) U.S. Cl.
CPC ................................... A61F 11/00 (2013.01)
(58) Field of Classification Search
None
See application file for complete search history.

(56) References Cited

U.S. PATENT DOCUMENTS 10,758,165 B2 * 9/2020 Hauptmann .......... A61M 21/00
2001/0051776 A1 * 12/2001 Lenhardt .................. A61N 7/00
601/2

2006/0093997 A1 * 5/2006 Kearby ................ G09B 21/009
381/60
2008/0064993 A1 * 3/2008 Abolfathi ............... H04R 25/75
601/47
2016/0005320 A1 * 1/2016 deCharms .............. G09B 19/00
434/236
2017/0143550 A1 * 5/2017 Kilgard .................. G09B 23/28
2023/0404439 A1 * 12/2023 Tass ....................... A61B 5/123

OTHER PUBLICATIONS

Sedley W. et al., "An integrative tinnitus model based in sensory precision", published in Trends in Neurosciences, 2016, vol. 39, No. 12, p. 799-812, 14 pages, cited in Specification.
Vallat, R., "Pingouin: statistics in python", published in Journal of Open Source Software, 2018, vol. 3., No. 31, p. 1026, 1 page, cited in the Specification.

* cited by examiner

*Primary Examiner* — Timothy A Stanis
*Assistant Examiner* — Thomas Z Chang
(74) *Attorney, Agent, or Firm* — HSML P.C.

(57)         ABSTRACT
A method for treating tinnitus includes the steps of: determining a tinnitus frequency of a patient; selecting a plurality of therapeutic tones which is a descending Shepard scale that includes the tinnitus frequency of the patient and other frequencies ranging from an octave higher than the tinnitus frequency to an octave lower than the tinnitus frequency; and subjecting the patient to several cycles of a stimulation pulse training in which the patient listens to the therapeutic tones played repetitively with a pause between every two cycles, each of the therapeutic tones being played for a time period of 500 milliseconds, one of the therapeutic tones matching the tinnitus frequency of the patient occurring randomly once after stimulus at the beginning of the pause in every four cycles, so as to reduce the patient's perception to tinnitus.

7 Claims, 1 Drawing Sheet

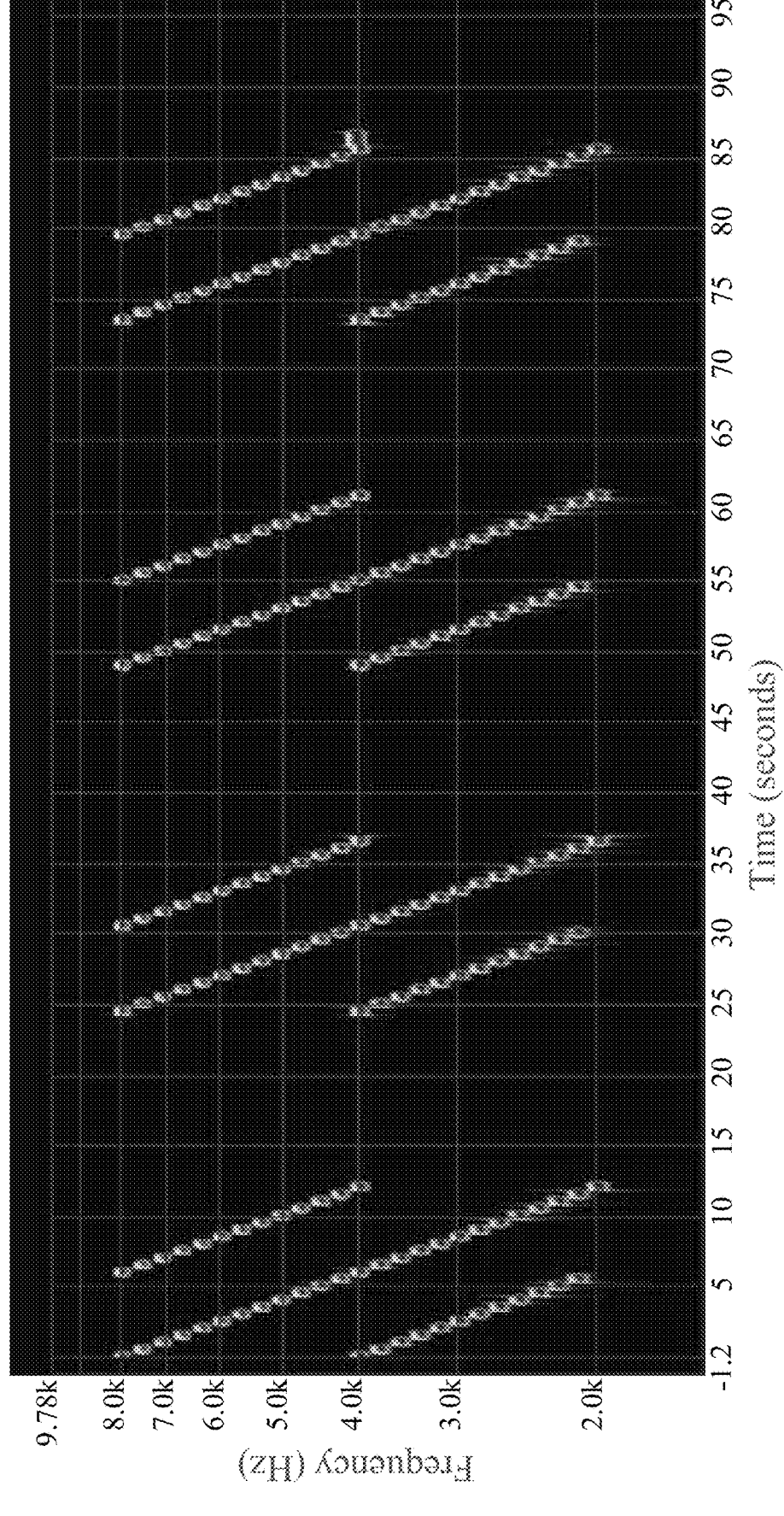

METHOD FOR TREATING TINNITUS

CROSS-REFERENCE TO RELATED APPLICATION

This application claims the benefit of U.S. Provisional Patent Application No. 63/329,801, filed on Apr. 11, 2022, which is incorporated by reference herein in its entirety.

FIELD

The present disclosure relates to a method for treating tinnitus.

BACKGROUND

Tinnitus is the perception of sound in the absence of exogenous sound stimulation. While often described as a ringing, tinnitus may also sound like buzzing, clicking, whirring, hissing or roaring. Continuous perception to tinnitus can lead to sleep disturbance, poor concentration, distress, depression, and anxiety. Consequently, restrictions caused by tinnitus might result in reduction in a patient's quality of life because of difficulties at work, at home, and in social relationships.

There have been many attempts made to treat or cure tinnitus, however, no treatment or intervention offers a completely satisfactory solution. At present, clinical management of tinnitus involve psychoeducation or counseling, relaxation techniques, and use of sound therapy. In recent decades, sound therapy which uses sound stimulation to mask or suppress tinnitus or to disrupt neural activity that causes tinnitus, and which is non-invasive and readily accepted by patients, has become a central part of the clinical management of tinnitus. However, implementation of sound therapy usually takes a long period of time and offers little immediate sense of relief from tinnitus.

Sedley W. et al., in an article entitled "An integrative tinnitus model based in sensory precision" published in *Trends in Neurosciences,* 2016, Vol. 39, No. 12, p. 799-812, proposes a hypothesis based on the Bayesian brain theory to explain the mechanism of tinnitus formation. In the article, the authors discloses that a 'tinnitus precursor' is driven by generation of an ascending prediction error by downstream neurons to the upstream neurons in the auditory pathway, and upon receiving the ascending prediction error, the upstream neurons generate a wrong descending prediction to the downstream neurons, such that the ascending and descending neuronal signals are matched to complete the feedback control, thereby resulting in perception of tinnitus. However, such hypothesis has an abstract meaning, and is yet to be entirely verified.

The applicants, based on such hypothesis and noting that Shepard scale had not been reported to be used in sound therapy for treating patients diagnosed with tinnitus, propose use of the Shepard scale in sound therapy so as to reduce the patients' perception to tinnitus.

SUMMARY

Therefore, an object of the present disclosure is to provide a method for treating tinnitus which can alleviate at least one of the drawbacks of the prior art.

According to the present disclosure, the method for treating tinnitus includes the steps of:

(a) determining a tinnitus frequency of a patient;

(b) selecting a plurality of therapeutic tones based on the tinnitus frequency of the patient, the plurality of therapeutic tones being a descending Shepard scale which includes the tinnitus frequency of the patient and other frequencies ranging from an octave higher than the tinnitus frequency to an octave lower than the tinnitus frequency; and (c) subjecting the patient to several cycles of a stimulation pause training in which the patient listens to the therapeutic tones played repetitively with a pause between every two cycles, one of the therapeutic tones matching the tinnitus frequency of the patient occurring randomly once after stimulus at the beginning of the pause in every four cycles, so as to reduce the patient's perception to tinnitus.

In the method for treating tinnitus, each of the therapeutic tones is played for a time period of 500 milliseconds.

BRIEF DESCRIPTION OF THE DRAWINGS

Other features and advantages of the present disclosure will become apparent in the following detailed description of the embodiment(s) with reference to the accompanying drawings. It is noted that various features may not be drawn to scale.

FIG. 1 is a spectrogram showing four continuous cycles of a hypothetical stimulation pulse training in which therapeutic tones are repetitively played as a descending Shepard scale.

DETAILED DESCRIPTION

Before the present disclosure is described in greater detail, it should be noted that if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The applicants, based on the hypothesis mentioned in the aforesaid Background section, conducted a stimulation pulse training in which therapeutic tones, in the form of a descending Shepard scale serving as a sound stimulus, are repetitively played to a patient diagnosed with tinnitus, so as to give the patient, the illusion that the frequency of the sound stimulus is getting lower and lower, thereby reducing the tinnitus frequency.

To be specific, in the stimulation pulse training, the patient is subjected to listen to the descending Shepard scale so as to give him/her the impression that the therapeutic tones heard have continuous reduction in frequency, and when playing of the descending Shepard scale stops, the patient would still be expected to listen to the descending Shepard scale in which the therapeutic tones have continuous reduction in frequency. At this point, if the patient unexpectedly heard one of the therapeutic tones which has a frequency matching to his/her tinnitus frequency, a "conflict" (i.e., between the therapeutic tones having continuous reduction in frequency and the tinnitus frequency of the patient) occurring would be utilized to alter the specific prediction errors (i.e., wrong neuronal signals), so as to reduce the patient's perception to tinnitus.

Therefore, the present disclosure provides a method for treating tinnitus, which includes the following steps (a) to (c).

In step (a), a tinnitus frequency of a patient is determined.

In step (b), a plurality of therapeutic tones is selected based on the tinnitus frequency of the patient. The plurality of therapeutic tones is a descending Shepard scale which includes the tinnitus frequency of the patient and other frequencies ranging from an octave higher than the tinnitus frequency to an octave lower than the tinnitus frequency.

In step (c), the patient is subjected to several cycles of a stimulation pulse training in which the patient listens to the therapeutic tones played repetitively with a pause between every two cycles. Each of the therapeutic tones is played for a time period of 500 milliseconds. One of the therapeutic tones matching the tinnitus frequency of the patient occurs randomly once after stimulus at the beginning of the pause in every four cycles, so as to reduce the patient's perception to tinnitus.

According to the present disclosure, the term "therapeutic tone" may be used interchangeably with "Shepard tone", and refers to a sound consisting of superposition of sine waves separated by octaves. When the bass pitch of the Shepard tone is played moving upward to downward, such Shepard tone is referred to as "a Shepard scale", which is a sound effect that creates an auditory illusion in listeners. As used herein, the term "descending Shepard scale" may be generated, for example, by simultaneously and cyclically playing multiple descending scales that are each separated from the closest neighboring scale(s) by one octave.

According to the present disclosure, after step (b) and before step (c), an appropriate intensity (i.e., sound volume) for each of the therapeutic tones is selected.

In certain embodiments, the descending Shepard scale includes 25 variants of the therapeutic tones having different frequencies.

In certain embodiments, in step (c), the pause between every two cycles lasts for a time period of 12.5 seconds.

In certain embodiments, the therapeutic tones are played using a sound therapy device. An example of the sound therapy device may include, a portable music player equipped with wired headphones, but is not limited thereto.

According to the present disclosure, the method is implemented for a time period of 2 weeks.

In certain embodiments, the method is implemented every day for a time period of at least 1 hour.

In an exemplary embodiment, the method is implemented twice every day, and each implementation is not less than 30 minutes.

The present disclosure will be described by way of the following examples. However, it should be understood that the following examples are intended solely for the purpose of illustration and should not be construed as limiting the present disclosure in practice.

EXAMPLES

Example 1. Evaluation of the Effect of Sound Therapy in the Form of a Descending Shepard Scale in Improvement of Tinnitus

Experimental Subjects

Patients with tinnitus, who were followed and treated at the Department of Otolaryngology, National Cheng Kung University Hospital, Tainan, Taiwan, were enrolled as participants in the following experiments. Each of the participants meets the following nine conditions: (i) age was over 20 years old; (ii) diagnosed with subjective tinnitus and bilateral tinnitus; (iii) perception to tinnitus persisted for more than 6 months; (iv) no mental-, emotional- and health-related disorders which prevent participation; (v) no history of neurological or cognitive disorder; (vi) not conscious of hearing impairment or communication impairment; (vii) able to understand the content of questionnaire and provide clear response thereto; (viii) Meniere's disease, acoustic neuroma and other diseases affecting outer ear and middle ear had been ruled out; and (ix) objective tinnitus and auditory hypersensitivity had been ruled out.

Experimental Procedures

A. Determination of Tinnitus Frequency and Treatment of Tinnitus Using Therapeutic Tones The participants (n=40) were randomly divided into 2 groups, i.e., an experimental group and a control group, in which the number of participants in each group is 20. The experimental group and the control group were subjected to a sound therapy for treatment of tinnitus as described below.

First, each participant in the experimental group and the control group was subjected to a pure-tone audiometry and a tinnitus psychoacoustic measurement. The pure tone audiometry is a hearing test routinely performed using pure tone stimuli to identify hearing threshold level of the participant so as to determine the degree, type and configuration of hearing loss. The tinnitus psychoacoustic measurement is performed to determine the participant's subjective and behavioural perception to tinnitus.

To be specific, in the pure tone audiometry, each participant was subjected to listen to pure tone stimuli with different pitches and loudness played on a pure tone audiometer using air conduction earphone or bone conduction earphone, and then the participant's hearing threshold level were measured in accordance with the participant's response after listening. A pure tone may be defined as a presentation of a single frequency that exhibits no harmonic distortions. The pure tone stimuli transmitted using air conduction earphone have frequencies ranging from 250 Hz to 8000 Hz, whereas the pure tone stimuli transmitted using bone conduction earphone have frequencies ranging from 500 Hz to 4000 Hz. Each pure tone stimulus lasted for a time period ranging from 1 second to 2 seconds. The pure tone stimuli has an initial intensity (i.e., sound volume) of 30 dB at a given frequency, which would be reduced to 10 dB if the participant provides response, and if the participant did not respond, the intensity will be increased by 5 dB each time for a total 10 times until the participant provides greater than 50% response to the pure tone stimuli. The intensity of the pure tone stimuli, at which greater than 50% response was recorded, was deemed the hearing threshold at such intensity.

The tinnitus psychoacoustic measurement includes a tinnitus pitch matching test and a loudness matching test, and was performed using pure tone or narrow-band noise as a sound stimulus based on the participant's description of tinnitus. Before performing the tinnitus pitch matching test, the test ear would be selected according to the reported location of the perceived tinnitus. If the reported location of the perceived tinnitus is unilateral or lateral to one side of the participant's head, the ipsilateral ear would be selected as the test ear. However, if the reported location of the perceived tinnitus is neither unilateral nor lateral to one side of the participant's head, the ear with better hearing would be selected as the test ear. In the case where there is no difference in the hearing ability between two ears, the test ear would be randomly selected.

The tinnitus pitch matching test was performed to determine the frequency of a sound stimulus that is closest to the tinnitus frequency of the participant. The sound stimulus of the tinnitus pitch matching test has two separate initial frequencies of 1000 Hz and 8000 Hz. Each participant was required to select one of the two initial frequencies (i.e., 1000 Hz or 8000 Hz) which was closer to his/her tinnitus frequency, and then the range of frequency of the sound stimulus was gradually narrowed from the chosen initial frequency until a specific frequency of the sound stimulus closest to or matches the tinnitus frequency of the participant was identified.

After tinnitus pitch had been matched to the tinnitus frequency for the first time, the experimental group was subjected to several cycles of a stimulation pulse training in which each participant is required to listen to therapeutic tones played in the form of a descending Shepard scale, which includes one therapeutic tone having a frequency similar to the tinnitus frequency of the participant and other therapeutic tones having frequencies ranging from an octave higher than the tinnitus frequency of the participant to an octave lower than the tinnitus frequency of the participant. The control group were subjected to the same stimulation pulse training, except that each of the therapeutic tones of the descending Shepard scale was played at two-and-a half octave lower than the pitch of the tinnitus frequency matched. The descending Shepard scale includes 25 variants of the therapeutic tones having different frequencies, and each of the therapeutic tones was played for a time period of 500 milliseconds, such that in one cycle of the stimulation pulse training, the descending Shepard scale was played for 12.5 seconds, followed by 12.5 seconds of pause. An exemplified spectrogram of one of the participants which illustrates the therapeutic tones being repetitively played as a descending Shepard scale are shown in FIG. 1.

The therapeutic tones were generated using Python code in Waveform audio file format, stored in a portable music player. The participants were subjected to listen to the therapeutic tones by turning on the portable music player. The intensity of the therapeutic tones was increased to the maximal intensity that is still comfortable to the participant. The stimulation pulse training was implemented for a time period of 2 weeks, and each participant was required to listen to the therapeutic tones for at least one hour every day in a quiet environment. Listening to the therapeutic tones might be conducted in two sessions every day, i.e., in the morning and evening, however, the time period for each session was not less than 30 minutes.

B. Clinical Tinnitus Questionnaire and Tinnitus Handicap Inventory

In this experiment, clinical tinnitus questionnaire (CTQ) and tinnitus handicap inventory (THI) written in traditional Chinese characters were used to obtain a general understanding of tinnitus, evaluate the degree of tinnitus, and the effect of the aforesaid sound therapy in each participant. The CTQ was filled out before the participants were subjected to the sound therapy, whereas the THI was filled out prior to and after completion of the sound therapy.

The content of the CTQ was directed to the description of tinnitus in terms of the symptoms, intensity, severity and medical history, as well as the hearing balance and health status of the participant, so as to facilitate understanding of the profile of tinnitus in each participant.

The THI includes three subscales for evaluation, i.e., functionality, emotion, and severity, and consists of 25 questions. There are three scale response options for each question, i.e., frequent (4 points), occasional (2 points), and not occurring (0 points), with a total score of 100 points. The total score of THI was used to evaluate the occurrence of tinnitus-related disorders, and the higher the total score of THI is, the more severe the impact of tinnitus on the participant's daily life is. The score levels of THI are categorized based on an article entitled "Guidelines for the grading of tinnitus severity: the results of a working group commissioned by the British Association of Otolaryngologists, Head and Neck Surgeons, 1999" by McCombe A. et al. which was published in *Clinical Otolaryngology & Allied Sciences,* 2001, Vol. 26, No. 5, p. 388-393. To be specific, a total score ranging 0 to 16 indicates slight or no handicap (Grade 1); a total score ranging from 18 to 36 indicates mild handicap (Grade 2); a total score ranging from 38 to 56 indicates moderate handicap (Grade 3); a total score ranging from 58 to 76 indicates severe handicap (Grade 4); and a total score ranging from 78 to 100 indicates catastrophic handicap (Grade 5).

For the participants of the experimental group and the control group who have been determined to have a THI score of equal to greater than 18 points (THI 18), the characteristics of tinnitus obtained based on the response provided in the CTQ and THI are summarized in Table 1 below.

C. Statistical Analysis

For participants with THI 18, the time period of treatment and the outcome of treatment on the THI was analyzed using two-factor mixed-design analysis of variance (ANOVA); changes in the THI score before and after treatment in each of the experimental group and the control group was analyzed using Wilcoxon signed-rank test; and the differences between the experimental group and the control group before and after changes in the THI score was analyzed using Mann-Whitney U test.

The aforesaid analyses were performed using Python's statistical package, i.e., Pingouin, based on an article entitled "Pingouin: statistics in python" by Vallat, R., which was published in Journal of Open Source Software, 2018, Vol. 3, No. 31, p. 1026. Statistical significance is indicated by $p<0.05$. The results showing the changes in characteristics of tinnitus before and after treatment in each of the experimental group and the control group are shown in Table 2 below, and the results showing the differences in characteristics of tinnitus between the experimental group and the control group are shown in Table 3 below.

Results:

A. Determination of Tinnitus Frequency and Treatment of Tinnitus Using Therapeutic Tones FIG. 1 is a spectrogram showing four continuous cycles of a hypothetical stimulation pulse training in which the therapeutic tones having different frequencies were repetitively played as a descending Shepard scale. As shown in FIG. 1, two therapeutic tones were played at each time point, and at the first time point, two therapeutic tones respectively having frequencies of 4000 Hz and 8000 Hz were simultaneously played, in which the tinnitus frequency was assumed to be 4000 Hz. After the stimulus and at the beginning of the pause of the fourth cycle in the stimulation pulse training, one of the therapeutic tones of the descending Shepard scale had a frequency of 4000 Hz which matched the tinnitus frequency. It should be noted that spectrograms showing the therapeutic tones played as the descending Shepard scales for participants of the experimental group and control group had the same pattern as that shown in FIG. 1, except that the frequency of the therapeutic tones first played and the range of frequency of other therapeutic tones of the descending Shepard scale in each cycle of the stimulation pulse training were different for each participant.

B. Clinical Tinnitus Questionnaire and Tinnitus Handicap Inventory the tinnitus pitch in the experimental group, suggesting that the longer the time period of treatment is, the better the outcome of treatment is.

Taken together, the results indicate that by subjecting the patient to repetitively listen to therapeutic tones played as descending Shepard scale which includes the tinnitus frequency of the patient and other frequencies ranging from an

TABLE 1

|  | Experimental group (n = 11) | | Control group (n = 14) | |
| --- | --- | --- | --- | --- |
|  | Baseline | Follow-up visit | Baseline | Follow-up visit |
| Age (years) | 54.4 ± 9.4 | | 58.2 ± 11.9 | |
| Gender (male/female) | 4/7 | | 7/7 | |
| Mean hearing threshold (0.25-8 kHz, dB HL) | 24.2 ± 9.5 | | 18.7 ± 7.7 | |
| THI scores | 41.4 ± 19.9 | 35.4 ± 19.5 | 39.8 ± 20.9 | 40.7 ± 20.3 |
| Tinnitus intensity (dB SL) | 14.3 ± 10.5 | 12.3 ± 9.7 | 12.2 ± 13.6 | 8.8 ± 8.6 |
| Tinnitus pitch (kHz) | 4.6 ± 3.8 | 3.9 ± 2.5 | 4.3 ± 2.7 | 4.8 ± 2.6 |

Data are presented as mean + SD except in the case of gender.
THI = Tinnitus Handicap Inventory;
SD = standard deviation;
dB HL = decibel hearing level
dB SL = decibel sensation level (number of decibels above the hearing threshold level of sound stimulus)

C. Statistical Analysis

TABLE 2

|  |  | Experimental group (n = 11) | Control group (n = 14) |
| --- | --- | --- | --- |
| THI score | Change from baseline [mean (SD)] | −6.00 (6.98) | −0.85 (7.26) |
|  | p value (change from baseline) | 0.007** | 0.55 |
| Tinnitus pitch | Absolute value of the change from baseline [mean % (SD)] | 67.83 (65.52) | 20.88 (28.10) |
|  | p value (change from baseline) | 0.0009*** | 0.0014** |

The symbols "" and "*" represent $p < 0.01$ and $p < 0.001$, respectively.

As shown in Table 2, there is a significant change in the THI score for the experimental group before and after treatment, however, for the control group, no significant change was noted in the THI score before and after treatment. To be specific, in comparison with the control group, the decrease in the THI score after treatment was greater in the experimental group, suggesting that the impact of tinnitus on the daily life of the participants in the experimental group was less severe compared with that of the control group. In addition, although there is a significant change in the tinnitus pitch before and after treatment for both of the experimental group and the control group, the degree of change in the tinnitus pitch of the experimental group was greater compared to that of the control group.

TABLE 3

|  |  | p value (comparison to control group) |
| --- | --- | --- |
| THI score | Change from baseline | 0.02* |
| Tinnitus pitch | Absolute value of the change from baseline | 0.01* |

The symbol "*" represents $p < 0.05$.

As shown in Table 3, in comparison with the control group, there is a significant interaction of the time period of treatment and the outcome of treatment on the THI score and octave higher than the tinnitus frequency to an octave lower than the tinnitus frequency, the THI scores of the patient can be significantly improved, and hence, the method for treating tinnitus of the present disclosure is expected to be effective in reducing the patient's perception to tinnitus.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, FIGURE, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is(are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for treating tinnitus, comprising the following steps in order:

(a) determining a tinnitus frequency of a patient by conducting a tinnitus pitch matching test, in which the patient selects an initial frequency of a sound stimulus that is closer to the tinnitus frequency of the patient, and then a range of frequency of the sound stimulus is gradually narrowed from the initial frequency selected by the patient until a specific frequency of the sound stimulus matching the tinnitus frequency of the patient is identified;

(b) selecting a plurality of therapeutic tones based on the tinnitus frequency of the patient, the plurality of therapeutic tones being a descending Shepard scale which includes the tinnitus frequency of the patient and other frequencies ranging from an octave higher than the tinnitus frequency to an octave lower than the tinnitus frequency; and (c) subjecting the patient to several cycles of a stimulation pulse training in which the patient listens to the therapeutic tones played repetitively with a pause between every two cycles, one of the therapeutic tones of the descending Shepard scale matching the tinnitus frequency of the patient occurring randomly once after stimulus and at the beginning of the pause in every four cycles, so as to reduce the patient's perception to tinnitus, wherein each of the therapeutic tones is played for a time period of 500 milliseconds.

2. The method as claimed in claim 1, wherein the descending Shepard scale includes 25 variants of the therapeutic tones.

3. The method as claimed in claim 2, wherein the pause between every two cycles lasts for a time period of 12.5 seconds.

4. The method as claimed in claim 1, wherein the therapeutic tones are played using a sound therapy device.

5. The method as claimed in claim 1, which is implemented for a time period of 2 weeks.

6. The method as claimed in claim 1, which is implemented every day for a time period of at least 1 hour.

7. The method as claimed in claim 1, wherein in step (a), the initial frequency is selected from 1000 Hz and 8000 Hz.

* * * * *